United States Patent
Hörle et al.

(10) Patent No.: US 9,889,048 B2
(45) Date of Patent: Feb. 13, 2018

(54) ABSORBENT CORE

(71) Applicant: SCA Hygiene Products AB, Göteborg (SE)

(72) Inventors: Magdalena Hörle, Göteborg (SE); Angelica Burvall, Bollebygd (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 15/308,847

(22) PCT Filed: May 15, 2014

(86) PCT No.: PCT/SE2014/050588
§ 371 (c)(1),
(2) Date: Nov. 4, 2016

(87) PCT Pub. No.: WO2015/174895
PCT Pub. Date: Nov. 19, 2015

(65) Prior Publication Data
US 2017/0071798 A1 Mar. 16, 2017

(51) Int. Cl.
*A61F 13/15* (2006.01)
*A61F 13/472* (2006.01)
(Continued)

(52) U.S. Cl.
CPC .. *A61F 13/47245* (2013.01); *A61F 13/15617* (2013.01); *A61F 13/15804* (2013.01);
(Continued)

(58) Field of Classification Search
CPC ...... A61F 13/56; A61F 13/511; A61F 13/514; A61F 13/45; A61F 13/4704;
(Continued)

(56) References Cited

U.S. PATENT DOCUMENTS

| 2,408,508 | A | | 10/1946 | Canavan |
| D234,162 | S | * | 1/1975 | Anderson ............ D24/125 |

(Continued)

FOREIGN PATENT DOCUMENTS

| DE | 29915071 U1 | 2/2000 |
| EP | 0159671 A2 | 10/1985 |

(Continued)

OTHER PUBLICATIONS

U.S. Appl. No. 15/308,849, filed Nov. 4, 2016, Magdalena Hörle et al.

(Continued)

*Primary Examiner* — Jacqueline Stephens
(74) *Attorney, Agent, or Firm* — Drinker Biddle & Reath LLP

(57) ABSTRACT

An absorbent core, intended for use in an absorbent product such as a panty liner, is disclosed, comprising an absorbent material and a superabsorbent material. The core has a first extension in a longitudinal direction and a second extension in a transverse direction, and a longitudinal central line extending through the core, located between a first longitudinal portion and a second longitudinal portion. The first and second longitudinal portions are symmetric about the longitudinal central line. The core has a head portion, an intermediate portion and a rear portion extending in a longitudinal direction of the core. The head portion includes mirror imaged first circular segment portions and first edge lines to which the circular segment portions transition. The intermediate portion includes mirror imaged first convex edge portions. The rear portion includes second edge lines tapering towards a rear end and the central line of the core in an angle.

12 Claims, 1 Drawing Sheet

(51) Int. Cl.
    *A61F 13/45*     (2006.01)
    *A61F 13/53*     (2006.01)
    *B29C 43/24*     (2006.01)
    *A61F 13/47*     (2006.01)
    *B29K 1/00*     (2006.01)
    *B29L 31/48*     (2006.01)

(52) U.S. Cl.
    CPC ............ *A61F 13/45* (2013.01); *A61F 13/472* (2013.01); *A61F 13/53* (2013.01); *B29C 43/24* (2013.01); *A61F 2013/4708* (2013.01); *A61F 2013/530007* (2013.01); *A61F 2013/530481* (2013.01); *A61F 2013/530802* (2013.01); *B29K 2001/00* (2013.01); *B29L 2031/4878* (2013.01)

(58) Field of Classification Search
    CPC ............ A61F 13/4708; A61F 13/15804; A61F 13/15617; A61F 13/53; A61F 13/472; A61F 13/147254; A61F 13/47254; A61F 2013/530802; A61F 2013/830007; A61F 2013/530481
    See application file for complete search history.

(56) References Cited

U.S. PATENT DOCUMENTS

| | | |
|---|---|---|
| 6,350,257 B1 | 2/2002 | Björklund et al. |
| 6,632,210 B1 | 10/2003 | Glasgow et al. |
| 6,965,058 B1 | 11/2005 | Raidel et al. |
| 2008/0103468 A1 | 5/2008 | Elfsberg et al. |
| 2009/0292268 A1 | 11/2009 | Bagger-Sjöbäck et al. |
| 2010/0152687 A1 | 6/2010 | Carlozzi |
| 2017/0071799 A1 | 3/2017 | Hörle et al. |

FOREIGN PATENT DOCUMENTS

| | | |
|---|---|---|
| EP | 0670153 A1 | 9/1995 |
| EP | 1138294 A1 | 10/2001 |
| EP | 1260205 A2 | 11/2002 |
| EP | 1757257 A2 | 2/2007 |
| EP | 1994917 A1 | 11/2008 |
| GB | 2282541 A | 4/1995 |
| WO | WO-97/39713 A1 | 10/1997 |
| WO | WO-99/25282 A1 | 5/1999 |
| WO | WO-01/35888 A1 | 5/2001 |
| WO | WO-2007/069957 A1 | 6/2007 |

OTHER PUBLICATIONS

Extended European search report dated Oct. 24, 2017 issued in corresponding European patent application No. 14 89 2150 (7 pages).

Extended European search report dated Oct. 4, 2017 issued in related European patent application No. 14 891 809.7 (7 pages).

* cited by examiner

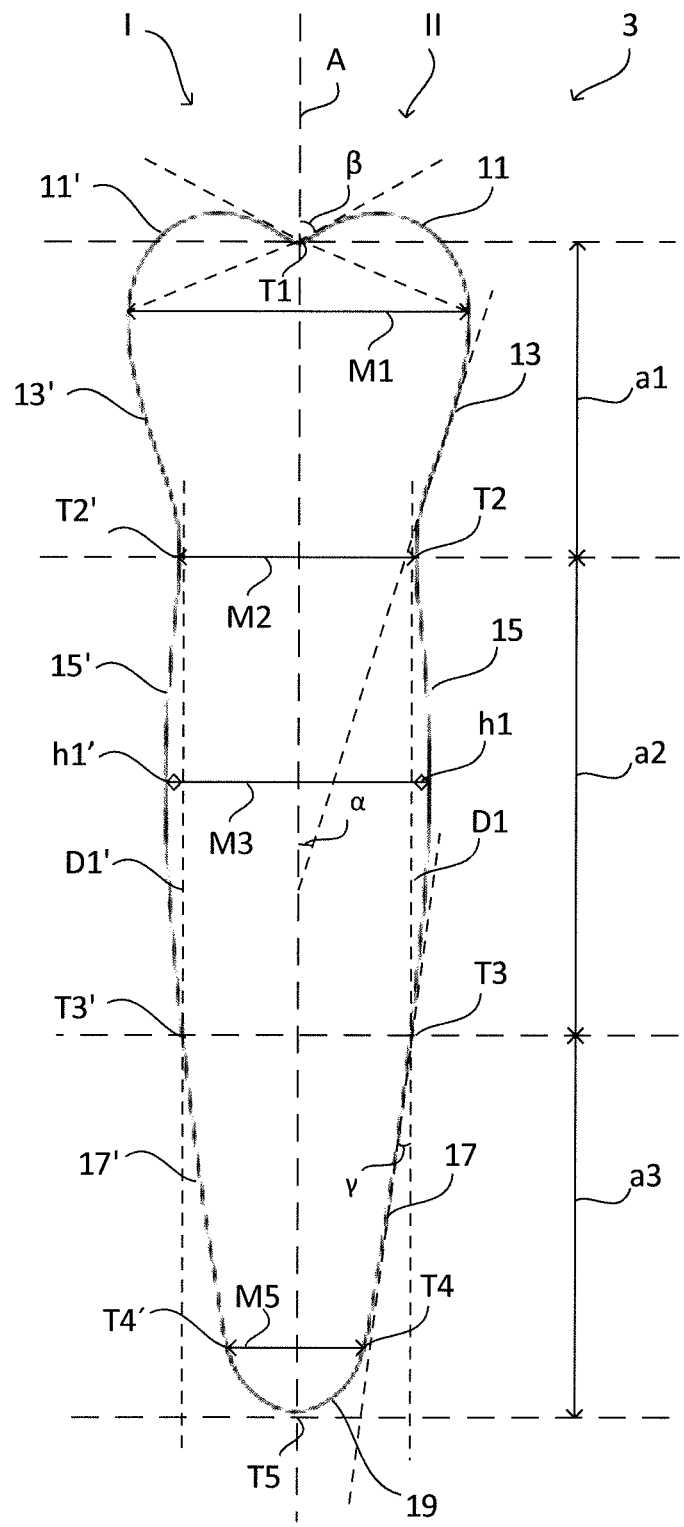

ABSORBENT CORE

CROSS-REFERENCE TO PRIOR APPLICATION

This application is a §371 National Stage Application of PCT/SE2014/050588 filed May 15, 2014, which is incorporated herein in its entirety.

TECHNICAL FIELD

The present disclosure relates to an absorbent core intended for use in an absorbent product such as a panty liner. The core includes an absorbent material with absorbent characteristics and a superabsorbent material. The core has a first extension in a longitudinal direction and a second extension in a transverse direction. The core has a longitudinal central line extending through the core, located between a first longitudinal portion and a second longitudinal portion. The first and second longitudinal portions are symmetric about the longitudinal central line. The core has a head portion, an intermediate portion and a rear portion extending in a longitudinal direction of the core.

The disclosure also relates to a process for the production of the absorbent core.

BACKGROUND

Panty liners are absorbent products that are used to absorb small amounts of bodily fluids such as urine and blood. Panty liners are smaller in size than sanitary towels or incontinence pads and are intended to be used for everyday freshness and to protect lingerie, i.e. panties or briefs. There are several kind of briefs on the market today: traditional briefs that have a crotch portion that is relatively broad, hipster-type of briefs that have a relatively narrow crotch portion and thong-type briefs that have a very narrow crotch portion followed by an even narrower rear portion so as to expose all or a significant portion of the buttocks of the user. Due to many different brief models it has been difficult in the prior art to optimize the shape and size of the panty liners such that a reliable protection is obtained while the panty liner is comfortable to wear and discreet. The optimization of the shape and size of the core of a panty liner follows with the problem to optimize the shape and size of the panty liners.

There have been several attempts in the prior art to solve problems with adapting the absorbent products to thong-type briefs. For example, EP 1757257 A2 and/or EP 1138294, respectively, disclose panty liners including a core which is adaptable to thong-type briefs. However, while these products may be adaptable to thong-type briefs, they do not provide an optimal comfort and feeling of secure protection when used with traditional briefs or with hipster-type briefs, since the core does not have a shape that conforms to the anatomy of the user or a shape to be adapted to that kind of underwear. Thus, there is a need for an absorbent core intended for use in an absorbent product such as a panty liner that can be worn with different types of underwear while optimal comfortability, adaptation to the anatomy of the wearer and protection can be provided.

SUMMARY

It is desired to provide an absorbent core intended for use in an absorbent product such as a panty liner, which provides for optimal comfort, adaptation to the anatomy of the wearer and protection while it can be used with different kinds of briefs or underwear. Thus, it is possible to avoid the previously mentioned problems.

Also disclosed is an absorbent core, intended for use in an absorbent product such as a panty liner. The core includes an absorbent material with absorbent characteristics and a superabsorbent material. The core has a first extension in a longitudinal direction and a second extension in a transverse direction. The core has a longitudinal central line extending through the core and located between a first longitudinal portion and a second longitudinal portion. The first and second longitudinal portions are symmetric about the longitudinal central line. The core has a head portion, an intermediate portion and a rear portion extending in a longitudinal direction of the core. The head portion includes, in the respective first and second longitudinal portions, mirror imaged first circular segment portions extending in a longitudinally forward direction of the core from a first transition point, located on the central line between the circular segment portions, in an acute angle β between the central line and a tangent at a point of transition point in respect of the circular segment portion, and mirror imaged first edge lines, to which the circular segment portions transition, tapering towards the intermediate portion and towards the central line of the core in an angle α being from 15-45°, and wherein the first edge lines taper to a second transition point located between the head portion and the intermediate portion.

The intermediate portion includes, in the respective first and second longitudinal portions, mirror imaged first convex edge portions extending between the second transition points and third transition points which third transition points are located between the intermediate portion and the rear portion. The lengths of the convex edge portions in respect to the central line is from 50-60% of the total length of the central line of the core and have a maximum height of the arch in the transverse direction of the core of from 1-10 mm. The rear portion includes second edge lines tapering towards a rear end and the central line of the core in an angle δ being from 3-20°. The second edge lines taper to a fourth transition point from which the second edge lines transition to a rear end portion that joins the edge lines together. In particular embodiments, the rear end portion is semi-circular or has a shape of circular segment, thus providing a comfortable shape in use.

One advantage with the desired absorbent core is that the core is suitable for use in absorbent products such as a panty liner which can be used with many types of briefs, for instance thong-type briefs, traditional briefs and hipster-type briefs. Thus, the core can be a panty liner core. As used herein, the term "panty liner" means an absorbent product which is used for feminine hygiene and which is thinner and narrower than sanitary napkins. Panty liners absorb less liquid than sanitary napkins and are thus aimed for light bodily discharge and for everyday cleanliness. The shape of the absorbent core has been found to fit the various widths of the crotch portions of for instance thong-type briefs, traditional briefs and hipster-type briefs when used in an absorbent article while still providing a good absorption capacity, adaptation to anatomy of the wearer and consequently very good comfort.

The absorbent core can be of a unitary construction. As used herein, the term "unitary construction" means that the absorbent core is constructed from essentially one type of material, this being essentially the same material, or essentially the same combination of two or more materials throughout the absorbent core. Variations in density and concentration of the material may occur, but these are limited to those which may be obtained without incorporation of regions which have been formed separately and then physically joined to each other. For example, when the absorbent core includes a matrix of an absorbent material with absorbent characteristics, e.g. hydrophilic fibres, and superabsorbent material, the relative concentrations of superabsorbent material and fibres may be different in different parts of the core. The absorbent material could also be a hydrophobic material that has the capability to keep liquid within the structure of the material. However, when the construction is unitary, the absorbent core does not, for instance, include layers or laminates of different composition. Likewise, variations in the density or concentration of various components across the longitudinal direction, the transverse direction or the thickness direction of the absorbent core may occur, yet the core should not include areas or layers of different composition which are formed separately and later joined together.

The total length of the core between the first transition point and the rear end of the core may be from 100 to 150 mm, from 120 to 135 mm, or from 126 to 131 mm. This core length has been found to be optimal for use in panty liners, such that maximal protection can be provided while the core is invisible in most briefs.

The first maximum width of the core in the head portion before transition to the first tapering edge lines may be from 35-50 mm, or from 36 to 40 mm. This width provides for maximal protection and adaptation to anatomy of the wearer while the core does not extend outside the edges of the underwear.

The width of the core between the second transition points may be from 20-34 mm, or from 24 to 28 mm. In this way, a narrower portion is provided in the core which improves the adaptation to the wearer, e.g. to the thighs of the wearer. Also, the core is easier to fold in transverse direction in this narrower portion making the core easier to handle. Also, in this way the core follows the underwear behaviour when the underwear is pulled up.

The second maximum width of the core in the intermediate portion at the point of maximum height may be from 25 to 45 mm, or from 27 to 31 mm, the second maximum width being at least 1 mm broader than the width of the core between the second transition points. This wider portion increases the absorption capacity of the product while further improving the adaptation to the anatomy of the wearer.

The dimensions and the geometrical design of the core that follows with the dimensions have been found to advantageously ensure that the core can be placed in a desired location and cover the crotch portion of the briefs where discharge of for instance menstrual fluid or urine occurs regardless of the type of briefs worn by the user. The core according to embodiments herein remains intact within the crotch area of the brief independent of the brief type when used in an absorbent article, i.e. the core fits within the crotch region of each briefs type and is subjected to minimal amount of stress from the movements of the user. The length ensures that the core is long enough for an absorbent product including the core does not move away from the intended position in the crotch portion. The different widths of the core ensure that there is a high absorption capacity in the front of the core where discharge may take place. Further, the fact that the second maximum width of the core in the intermediate portion at the point of maximum height is at least 1 mm broader than the width of the core between the second transition points ensures that there is high absorption capacity also in the middle part of the core. This protects the crotch portion of the brief from becoming wet and also increases the total absorption capacity of the core.

The amount of the superabsorbent material may be from 10 to 30% by weight of the total weight of the absorbent core, or from 15 to 20% by weight. The amount of superabsorbent material ensures a good absorption capacity while maintaining a soft and comfortable core. The thickness of the core may be from 1.5 to 3.4 mm, or from 2.2 to 3.0 mm. The thickness of the core makes the core pliable and allows the core to easily follow the body of a wearer.

The density of the core may be from about 100 to 180 $kg/m^3$, or from 120 to 145 $kg/m^3$. An absorbent core according to embodiments herein is capable of handling of at least 5 ml of menstrual fluid and is therefore suitable for everyday freshness use.

The longitudinal extension of the head portion is about ¼ of the extension of the core, the extension of the intermediate portion is about ½ of the extension of the core and the extension of the rear portion is about ¼ of the extension of the core. These dimensions provide for an optimal shape for the core.

The core may include cellulosic fluff pulp, tissue, absorbent foam materials or absorbent nonwoven materials as the absorbent material. In particular embodiment, the core includes cellulosic fluff pulp, which is easy to process and thus makes the core easy to manufacture while very good absorption capacity can be provided.

A process for the production of an absorbent core. The process includes:
  a. providing a mat-forming wheel;
  b. providing a cellulosic fluff pulp as an absorbent material with absorbent characteristics and a superabsorbent material, and maintaining the absorbent material and the superabsorbent material inside the mat-forming wheel
  c. mounting an air-permeable mould having the shape of the core on to the wheel;
  d. rotating the wheel and drawing the absorbent material and the superabsorbent material into the mould and thereby form the core having the shape;
  e. expelling the core structure from the mould; and
  f. conveying the core structure through a calendar roll to compress the core structure to unitary construction.

By this process, the core may be easily produced, especially to the uniform structure that is desired.

The absorbent material and the superabsorbent material are drawn into the mould by means of vacuum arranged inside the rotating mat-forming wheel.

The core is expelled from the mould by means of an airflow arranged to blow outwardly from the interior of the mat-forming wheel.

The absorbent material is cellulosic fluff pulp provided in the form of a roll, wherein the step of providing absorbent material further includes conveying the roll of cellulosic fluff pulp to a grinding device to grind the material into fibrous pulp.

Mat-forming processes are for instance described in U.S. Pat. No. 4,765,780, SE 9401542-7 and EP 1253231 and WO 2010/015052.

BRIEF DESCRIPTION OF THE DRAWINGS

FIG. 1 schematically shows an example of an absorbent core according to an embodiment of the invention.

DETAILED DESCRIPTION OF PARTICULAR EMBODIMENTS

FIG. 1 is a schematic view of an absorbent core 3, viewed from the above. The core 3 includes an absorbent material with absorbent characteristics and a superabsorbent material. The core has a first extension in a longitudinal direction and a second extension in a transverse direction. The core has a longitudinal central line A extending through the core. The longitudinal central line A is located between a first longitudinal portion I and a second longitudinal portion II. The first and second longitudinal portions I; II are symmetric about the longitudinal central line A. The core has a head portion a1, an intermediate portion a2 and a rear portion a3 extending in a longitudinal direction of the core 3 from the front of the core 3 to the rear of the core 3. The longitudinal extension of the head portion a1 is about ¼ of the longitudinal extension of the core 3, the longitudinal extension of the intermediate portion a2 is about ½ of the longitudinal extension of the core 3 and the longitudinal extension of the rear portion a3 is about ¼ of the extension of the core 3.

The head portion a1 includes in the respective first and second longitudinal portions I; II mirror imaged first circular segment portions 11; 11' extending in a longitudinally forward direction of the core from a first transition point T1. A longitudinal forward direction of the core 3 is in the direction towards and over the head portion a1 of the core 3. The first transition point T1 is located on the central line A in the intersection between the circular segment portions 11, 11'. The first circular segment portions 11; 11' extend in the forward direction over the transition point T1 and from the transition point T1 in an acute angle β. β is defined as the angle between the central line A and a tangent line of the circular segment portions 11; 11', where the tangent line is the tangent line at the transition point T1 of the respective circular segment portions 11; 11'. The angle β may be for 30-70°, 40-60°, or 45-55° so as to obtain an optimal shape for the front portion of the core.

The head portion a1 further includes in the first and second longitudinal portions I; II mirror imaged first edge lines 13; 13', to which the circular segment portions 11; 11' transition directly or indirectly via a smooth curved connection. The core 3 has a first maximum width M1 in the head portion a1 before transition of the circular segment portions 11; 11' to the first tapering edge lines 13; 13'. The first maximum width M1 is from 35-50 mm, or from 36 to 40 mm to obtain high absorption while the shape of the core conforms to the anatomy of the user. The circular segment portions 11; 11' can transition to the first tapering edge lines 13; 13' at the first maximum width M1 of head section a1 or below the first maximum width M1 of the head section a1. It is important that M1 has a sufficient width to ensure that the core is comfortable in use. The width M1 should be sufficient to cover labia, while the width should be small enough not to extend outside the edges of the intended underwear. The width above has been found to fulfil these requirements. From the transition the first edge lines 13; 13' taper towards the intermediate portion a2 and towards the central line A of the core in an angle α, α being from 15-45°. A larger angle than 45° leads to a broad head portion which may not completely fit within the crotch portion of the brief. A smaller angle than 15° leads to a narrow head portion a1 which may not have enough absorption capacity or coverage to ensure that discharge of fluids does not reach the briefs. The first edge lines 13; 13' taper to second transition points T2, T2' located between the head portion a1 and the intermediate portion a2. The distance between the second transition points T2; T2' is the width M2 of the core 3. M2 is from 20-34 mm, or from 24 to 28 mm.

The intermediate portion a2 includes, in the respective first and second longitudinal portions I; II, mirror imaged first convex edge portions 15; 15' extending between the second transition points T2; T2' and third transition points T3; T3'. The third transition points T3; T3' are located between the intermediate portion a2 and the rear portion a3. The length of the convex edge portions 15; 15' in respect to the central line A is from 50-60% of the total length of the central line A of the core and have a maximum height h1; h1' of the arch in the transverse direction of the core of from 1-10 mm. The total length of the convex edges 15; 15' is thus determined by the distance D1; D1' between the second transition points T2; T2' and the third transition points T3; T3' in the direction along the central line A and the maximum height h1; h1'. The maximum height h1; h1' is measured from a longitudinally extending line coinciding with the distance D1; D1' to the highest point on the convex edges 15; 15'. The location of the maximum height h1; h1' coincides with the location of the second maximum width M3 of the intermediate portion a2. It is important that M3 has a sufficient width to ensure that maximum amount of the discharge lands on the core and not outside the core in use, while the width should be small enough not to extend outside the edges of the intended underwear. In this way leakage problems can be avoided. The convex edges 15; 15' further improve the adaptation of the core to the anatomy of the wearer, while absorption capacity is also improved. The transition between the first edge lines 13; 13' and the first convex edge portions 15; 15' can be a continuous, smooth transition. The transition between the first edge lines 13; 13' and the first convex edge portions 15; 15' can alternatively be a dis-continuous transition, i.e. a transition in which the first edge lines 13; 13' and the first convex edge portions 15; 15' form a notch at the transition.

The rear portion a3 includes second edge lines 17; 17' extending between the third transition points T3; T3' and fourth transition points T4; T4'. The second edge lines 17; 17' are essentially straight or slightly arched. The transition between the first convex edge portions 15; 15' and the second edge lines 17; 17' can be a continuous, smooth transition. The second edge lines 17; 17' taper towards a rear end T5 and the central line A of the core in an angle γ. The angle γ is defined as the angle between an extension of the distance D1 passing through transition point T3; T3' and a tangent line of the first convex edge portions 15; 15', where the tangent line is the tangent line at the transition point T3; T3' of the respective first convex edge portions 15; 15'. The angle γ may be for example 3-20°, 5-15°, or 7-11°. The second edge lines 17; 17' taper to a fourth transition point T4, T4' from which the second edge lines 17; 17' transition to a rear end portion 19 that joins the edge lines 17; 17' together. As shown in FIG. 1, the rear end portion 19 is semi-circular or has a shape of a circular segment. However, the end rear portion could have a straight line-shape connecting the second edge lines 17; 17'. The tapered rear portion a3 makes the core easy to adapt to different kind of briefs, such as thong-type briefs. The transition between the second edge lines 17; 17' and the semi-circular or circular segment rear end portion 19 can be a continuous, smooth transition. The total length of the core 3 between the first transition point T1 and the rear end T5 of the core 3 is from 100 to 150 mm, from 120 to 135 mm, or from 126 to 131 mm.

The absorbent core 3 is appropriately manufactured from a suitable fibre material in the form of natural or synthetic fibres with absorbent characteristics, or a mixture of natural fibres and synthetic fibres or other absorbent materials of a previously disclosed kind that are suitable for use in for example panty liners. In particular embodiments, the absorbent material of the core comprises or consists of cellulosic fluff pulp. The absorbent core 3 can also include a predetermined proportion, for example 10-30%, of superabsorbent material, that is to say polymer materials in the form of particles, fibres, flakes or the like, which possess the ability to absorb and chemically bind liquid equivalent to several times their own weight to form an aqueous gel. This imparts a very high liquid-absorbent capacity to the finished absorbent core 3 while maintaining a soft core for comfort.

The first and second portions I; II are designed and arranged such that they are symmetric in respect to each other about the longitudinal centre line A of the core. This is important so that the core lies symmetrically on the user's body when in use. By the expression "symmetric about the longitudinal centre line A" it is herein meant that each point in the first or second portions on one side of the longitudinal centre line A has a corresponding point in the opposing side of the longitudinal centre line A; the two points being related to each other by reflection in a plane located on the longitudinal centre line A. The first longitudinal portion located on one side of the longitudinal centre line A is therefore the mirror image of the second longitudinal portion located on the other side of the longitudinal centre line A.

The absorbent core 3 can have rounded edges for increased comfort.

Reference signs mentioned in the claims should not be seen as limiting the extent of the matter protected by the claims, and their sole function is to make claims easier to understand. The drawings and the description are to be regarded as illustrative in nature, and not restrictive.

The invention claimed is:

1. An absorbent core, intended for use in an absorbent product, comprising:
    an absorbent material with absorbent characteristics;
    a superabsorbent material;
    a first extension in a longitudinal direction;
    a second extension in a transverse direction;
    a longitudinal central line extending through the core and located between a first longitudinal portion and a second longitudinal portion, which first and second longitudinal portions are symmetric about the longitudinal central line; and
    a head portion, an intermediate portion, and a rear portion extending in a longitudinal direction of the core,
    wherein the head portion comprises, in the respective first and second longitudinal portions, mirror imaged:
    first circular segment portions extending in a longitudinally forward direction of the core from a first transition point, located on the central line between the circular segment portions, in an acute angle β between the central line and a tangent at the first transition point in respect of the circular segment portion; and
    first edge lines forming a portion of a periphery of the absorbent core, to which the circular segment portions transition, tapering towards the intermediate portion and towards the central line of the core in an angle α being from 15-45°, and wherein the first edge lines taper to a second transition point located between the head portion and the intermediate portion,
    wherein the intermediate portion comprises, in the respective first and second longitudinal portions, mirror imaged:
    first convex edge lines forming a portion of the periphery of the absorbent core extending between the second transition points and third transition points, which third transition points are located between the intermediate portion and the rear portion, wherein the length of the first convex edge lines in respect to the central line is from 50-60% of the total length of the central line and each of the first convex edge lines form convex portions having a maximum height of the arch formed by the first convex edge lines in the transverse direction of the core of from 1-10 mm; and
    the rear portion comprises second edge lines forming a portion of the periphery of the absorbent core tapering towards a rear end point and the central line in an angle γ being from 3-15°, and wherein the second edge lines taper to a fourth transition point from which the second edge lines transition to a rear end portion that joins the edge lines together.

2. The absorbent core according to claim 1, wherein the rear end portion is semi-circular or has a shape of a circular segment.

3. The absorbent core according to claim 1, wherein the core is of a unitary construction.

4. The absorbent core according to claim 1, wherein the total length of the core between the first transition point and the rear end point is from 100 to 150 mm.

5. The absorbent core according to claim 1, wherein a first maximum width of the core in the head portion before transition to the first edge lines is from 35-50 mm.

6. The absorbent core according to claim 1, wherein a second width of the core between the second transition points is from 20-34 mm.

7. The absorbent core according to claim 6, wherein a third maximum width of the core in the intermediate portion between points on the first convex edge portions having the maximum height is from 25 to 45 mm, the third maximum width being at least 1 mm greater than the second width.

8. The absorbent core according to claim 1, the superabsorbent material is present in an amount from 10 to 30% by weight of the total weight of the absorbent core.

9. The absorbent core according to claim 1, wherein the core has a thickness from 1.5 to 3.4 mm.

10. The absorbent core according to claim 1, wherein the core has a density from about 100 to 180 kg/m$^3$.

11. The absorbent core according to claim 1, wherein a longitudinal extension of the head portion is about ¼ of the longitudinal extension of the core, a longitudinal extension of the intermediate portion is about ½ of the longitudinal extension of the core, and a longitudinal extension of the rear portion is about ¼ of the longitudinal extension of the core.

12. The absorbent core according to claim 1, wherein the absorbent material comprises cellulosic fluff pulp, tissue, absorbent foam materials, or absorbent nonwoven materials.

* * * * *